United States Patent [19]
Coico et al.

[11] Patent Number: 4,921,667
[45] Date of Patent: May 1, 1990

[54] METHOD FOR AUGMENTING IMMUNE RESPONSE

[75] Inventors: Richard F. Coico, Larchmont; G. J. Thorbecke, Douglaston, both of N.Y.

[73] Assignee: New York University, New York, N.Y.

[21] Appl. No.: 15,074

[22] PCT Filed: Apr. 23, 1986

[86] PCT No.: PCT/US86/00939
§ 371 Date: Feb. 2, 1987
§ 102(e) Date: Feb. 2, 1987

[87] PCT Pub. No.: WO86/06490
PCT Pub. Date: Nov. 6, 1986

Related U.S. Application Data

[63] Continuation-in-part of Ser. No. 726,089, Apr. 23, 1985, abandoned.

[51] Int. Cl.$^5$ .................. A61K 39/00; C07K 13/00
[52] U.S. Cl. .................. 424/85.8; 530/387; 530/389; 435/29; 435/240.2; 424/85.2; 424/95; 424/101
[58] Field of Search .............. 424/85, 86, 85.2, 85.8, 424/95, 101; 514/2; 436/513; 530/380, 386, 387, 388, 389, 417; 435/29, 240.2

[56] References Cited
U.S. PATENT DOCUMENTS 4,490,289 12/1984 Stern ........................ 435/68
4,689,400 8/1987 Finkelman .................. 530/329

OTHER PUBLICATIONS

Coico et al., *J Exp. Med.*, vol. 162, pp. 1852-1861., Dec. 1985, "Physiology of Igd. Transfer of the . . . Helper Cell Populations".
Finkelman et al., *JImm*, vol. 129, pp. 638-646, "Polyclonal Activation of the Murine Immune System . . . IgD".
Cuchens et al., *J Tmm*, vol. 121(6) Dec. 1978, "The Effects of Anti-IgD on Serum Immunoglobulins, Antibody Production, and Immunoglobulin-Bearing Cells".
Xue et al., *J Exp Med.*, vol. 159, pp. 103-113, Jun. 1984, "Physiology of IgD Enhancement of Antibody Production".
Coico et al., *Nature*, vol. 316, Aug. 1985, pp. 744-746, "T Cells With Receptors for IgD".
Khorobrykh et al., *Biol Abst.*, 1978, vol. 66, No. 246264, "Effect of Antisera to Aggregated Mouse Immuno-Globulin on the Population of Lymphoid . . . Cells".

*Primary Examiner*—Robin L. Teskin
*Attorney, Agent, or Firm*—Darby & Darby

[57] ABSTRACT

Disclosed is a method for enhancing the ability for humoral immune response in a mammal comprising:
exposing lymphocytes histocompatible with the lymphocytes of said mammal to the presence of polymeric or aggregated delta-immunoglobulin at a concentration higher than that at which said lymphocytes would have been exposed while in the lymph or bloodstream of said mammal; and introducing said lymphocytes to the bloodstream or lymph of said mammal.

21 Claims, 1 Drawing Sheet

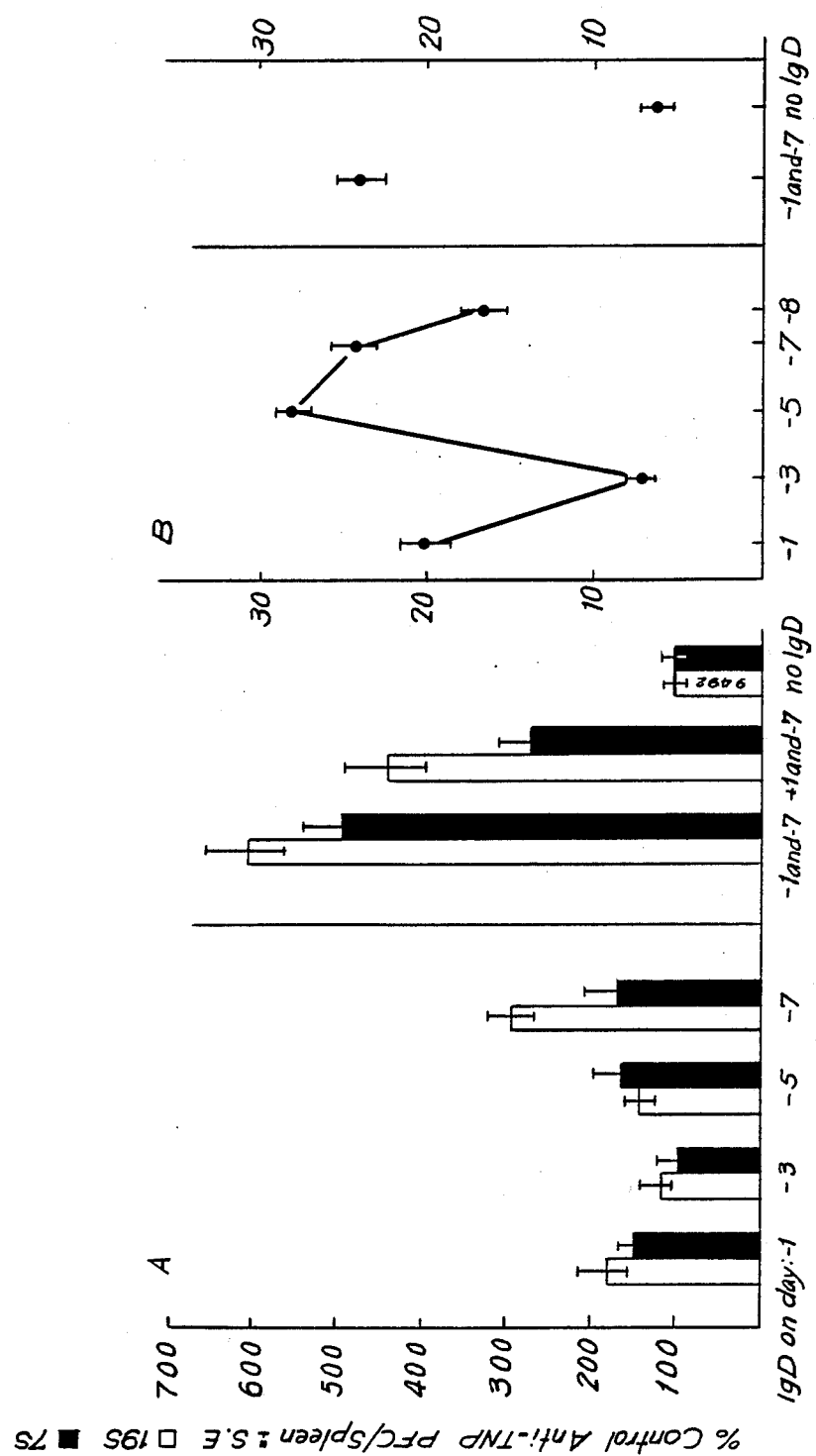

METHOD FOR AUGMENTING IMMUNE RESPONSE

The United States Government has rights to this invention by virtue of grants No. AI-11694 and No. AG-04980 and Training Grant No. CA-09161 from the Department of Health and Human Services.

This application is a continuation in part of application Ser. No. 726,089 filed 4-23-85 now abandoned.

FIELD OF THE INVENTION.

This invention relates to a method for increasing antibody production and enhancing humoral immune response. According to this method, delta-immunoglobulin (IgD) is used to induce lymphocytes (especially T cells) that initiate or mediate immunostimulatory action.

BACKGROUND OF THE INVENTION

IgD is one of five known classes of immunoglobulins. It is present on the surface of mature B cells (where it is co-expressed with IgM) but its serum levels are low. In contrast to other Ig isotypes, IgD is not secreted following antigenic stimulation of the B cells that bear it.

Although, apparently, surface IgD (sIgD) can function as a receptor for stimulation of B cells to enter the cell cycle, IgD has not been assigned a clear, specific function in immune response. At this time, more is known about what IgD does not do than what it does.

There are indications that IgD may play an important role in resistance to induction of antigen tolerance: see, Vitetta, E.S. and Uhr, J.W. *Science* 189:964 1975, who report that the B cells of young mice (that typically show tolerance) express only IgM, not IgD. The onset and increase of tolerance resistance parallels the ability of the B cells of the growing mouse to express IgD. The observed decrease in surface IgD of B cells subsequent to antigen stimulation is consistent with the tolerance resistance hypothesis.

Finkelman, F.D. et al. *J. Immunol.* 133:550, 1984 and *N.Y. Acad. Sci.* 399:316, 1982 have shown that administration to mice of goat anti-(mouse IgD) caused the B cells of the mice to produce significantly higher amounts of polyclonal IgG1 antibodies. The authors interpreted these results as indicating the existence of nonspecific T help in the mouse system. The authors also observed an apparent suppression of antibody production when they administered high levels of goat anti-(mouse IgD).

There is evidence of the existence of T-cell sub-populations that are isotype-specific for IgA, IgE, IgG and IgM both in humans and in mice. IgA-specific T cells ($T_a$)—but not $T_e$, $T_g$, or $T_m$—have been induced by IgA-secreting plasmacytomas. These $T_a$ cells have been studied extensively but have not been found to augment humoral immune responses.

In *Scand. J. Immunol.* 11:377–382, 1980, O. Sjoberg reported that a small percentage of normal human lymphocytes (0–6.5%) formed rosettes with IgD-coated latex particles. This is the earliest report known to the present inventors suggesting the existence of lymphoid cells with a receptor for IgD. However, the reported incidence of these cells does not exceed background levels for isolated peripheral blood leukocytes, which is what Sjoberg used in this study. Therefore, the results reported in this article are inconclusive. Moreover, the author does not suggest any therapeutic or other use for cells with IgD receptors.

IgD-producing plasmacytomas were discovered by Finkelman, F.D. et al. 1981 *J. Immunol.* 126:680, incorporated herein by reference. These plasmacytomas were induced by injecting Balb/c mice intraperitoneally with 0.5 ml of tetramethylpentadecane (pristane).

In Xue, B., et al., *J. Exp. Med* 159:103–113 (Jan. 1984) the authors (who include the present inventors) report the following observations for mice only:

(1) Mice bearing IgD-producing plasmacytomas or injected with IgD-containing whole ascites fluid from plasmacytoma-bearing mice exhibit enhanced antibody production upon subsequent challenge with antigen. This was observed for antibodies of both the IgM and the IgG isotype.

(2) Mice injected with purified IgD, showed an increase in IgM production only.

The authors postulated that the immunoaugmenting effect was due to T cells having a receptor for IgD that were elicited following injection of IgD.

The practical significance of the work reported in this article is limited for several reasons. First, the ability of IgD-plasmacytoma or IgD-plasmacytoma ascites fluid to stimulate IgG production cannot be used for therapeutic applications in humans. Introduction of tumor cells and ascites fluid from ascites tumor bearing mice would be hazardous to the recipients.

Second, increased production of IgM is not as desirable as that of IgG antibody, especially for long term immunity. The IgG isotype has a greater affinity for the antigen and a longer half-life.

It is clear from the above discussion that a more complete understanding of the nature and role of IgD is necessary. Therefore, a broad objective of this invention is to increase this understanding and to use it to develop therapeutic methods for the management or treatment of immune system disorders.

Another object of the present invention is to provide a safe and effective method for increasing the efficiency of immunization protocols, especially in terms of other isotypes in addition to IgM, such as IgG (7S) responses.

A more specific object of the present invention is to confirm the existence of (and to provide a convenient and safe method for inducing) T cells with receptors for IgD.

Another object is to provide a convenient and safe method for inducement of T cells that are able to stimulate the immune system to produce increased amounts of IgG, and to use such T cells in the management or treatment of mammals, including humans, with depressed immune systems.

Another object is to provide a method for enhancing antibody production.

Another object is to provide a method for augmenting or restoring humoral immune response, especially in immunosuppressed or immunocompromised mammalian hosts, but also in normal vaccinated hosts.

Another object is to provide a method for augmenting or restoring humoral immune response while limiting or eliminating the infusion of exogenous substances in these hosts.

Another object is to provide a method for testing immune competence.

These and other objects of the present invention will be apparent to those skilled in the art in light of the present description, accompanying claims and appended drawings.

BRIEF DESCRIPTION OF THE DRAWINGS

FIG. 1A shows the kinetics of IgD-induced enhancement antibody response to TNP-KLH.

FIG. 1B shows the kinetics of $T_d$ cell appearance following injection of IgD-containing ascites fluid.

SUMMARY OF THE INVENTION

The present inventors have now demonstrated that helper T cells with receptors for IgD ($T_d$) do in fact exist in humans and in mice.[1] Moreover, they found that a significant number of helper T cells capable of enhancing IgG antibody response can be induced by exposing T lymphocytes to IgD (including dimer and oligomer IgD) in vitro as well as in vivo. Surprisingly, subsequent introduction of these $T_d$ cells in the blood stream of a mammal is also accompanied by a significant increase in IgG (as well as IgM) antibody response.

[1] However, in order to avoid binding this application to any particular theory, $T_d$ shall mean not only T cells with a receptor for IgD, but also any T cells elicited as described herein that have the ability to enhance immune response in a recipient.

Thus, generation of the $T_d$ in the body of the target host is not required for immune response enhancement, but induced $T_d$ survive infusion in an untreated (naive) host and enhance immune responses in that host.

It is of course preferable that the infused $T_d$ be histocompatible with the recipient. The $T_d$ can be induced in vitro and, most preferably, they are obtained from the blood or lymph of the recipient.

The present inventors have also found that purified IgD is effective as an adjuvant that augments the immune responses of mammals, including humans, when administered in sufficient amounts simultaneously with and/or shortly prior to an antigen.

Surprisingly, repeated injections of isolated IgD (such as IgD isolated from serum or plasma of normal individuals) or purified from cultures (or ascites fluid of mice bearing IgD secreting hybridomas or plasmacytomas) further increase the augmentation of the immune response and cause an augmentation of the IgG antibody response although they do not appear to increase the number of $T_d$ cells more than the first injection. In fact, repeated injections of isolated IgD serve to augment IgG immune response even where a single injection has failed.

One aspect of the present invention is directed to a method for enhancing humoral immune responses in (and, especially, increasing the quantity of IgG antibody produced by) a mammal in response to antigenic stimulation of said mammal. This method comprises exposing lymphocytes to the presence of IgD in a quantity and for a period of time sufficient to activate helper T cell function in the mammal, such as will mediate enhancement of immune responses. Such exposure of lymphocytes to IgD preferably takes place in a manner avoiding introduction of undesirable substances in the body of the mammal, but may be combined with in vivo treatment of the mammal with IgD.

This can be done in several ways. First, it can be done by exposure of the lymphocytes to IgD in vitro followed by introduction of treated, washed lymphocytes into the mammal. In that case IgD-ascites fluid can be used as the incubation medium, since it will not be injected, or IgD-coated dishes can be used.

Second, it can be done in vivo by introduction into the mammal of an IgD-containing preparation that is suitable for administration in the mammal and does not contain physiologically undesirable substances. In order to augment the production of isotypes other than IgM, most notably IgG production, repeated administration of IgD (and/or administration of higher amounts than are necessary for augmenting IgM production) is necessary.

Third, it can be done in vivo followed by cell transfer. An IgD-containing preparation (sufficient to cause augmentation of IgG response upon antigenic stimulation) is administered to a donor mammal. Activated lymphocytes from the donor (preferably histocompatible with the recipient) are transferred to the recipient mammal.

Finally, helper T cell activation can be done by a combination of in vivo followed by in vitro treatment with IgD, as described above.

Still another aspect of the invention relates to a method for determining immunocompetence of a mammal by exposing T cells of said mammal to IgD at a concentration sufficient to elicit $T_d$ cells in a normal (immunocompetent) mammal of the same species, detecting the numbers of $T_d$ cells elicited with and without exposure to IgD, and comparing them to those of normal members of said species.

DETAILED DESCRIPTION OF THE INVENTION

A particular advantage of the method of the present invention is that $T_d$ induction can take place outside the recipient's body. Most preferably, $T_d$ induction takes place in vitro and the induced $T_d$ lymphocytes are the patient's own lymphocytes. Thus, the present method can avoid infusing any exogenous substance in the host.

The present invention is for use in enhancing humoral immune responses especially IgG antibody responses, ameliorating depressed immune responses (especially these secondary to such diseases as viral infections, lymphoma, and carcinoma) and depressed immune response caused by agents used in the treatment of these diseases, including (but not limited to) cytotoxic agents such as cortisone, vincristine, adriamycin, methotrexate, fluorouracil, cyclophosphamide, etc.

IgD is a naturally occurring substance that is present in the serum of normal mammals including humans in low amounts (normal human range: about 10 to 100 micrograms/ml with about 30 being most common). Therefore, repeated injections of purified IgD with the aim of augmenting the immune response are an important application of the present invention of in man, not only to restore immune response but also to serve as an adjuvant to enhance immune responses to vaccines and other immunogens. In the latter case administration of IgD would take place simultaneously with, and/or soon before, immunization.

IgD should preferably be used in polymeric or aggregated form. IgD-secreting tumor cells can be used as a source of IgD. IgD-secreting plasmacytomas are available from the National Cancer Institute (NCI) Tumor Bank, Rockville, Md. A mouse IgD-secreting B cell hybridoma (B1.8-delta) described by Neuberger, M.S. and Rajewski, K, *Proc. Nat'l Acad. Sci.* (USA) 78:1138, 1981 can also be used. This line secretes an IgD delta2/-lambda2 anti-(4-hydroxy-3-nitrophenyl) acetyl (NP) antibody. This IgD is much more effective for $T_d$ induction after interaction with NP-protein (antigen).

Culture media from, or ascites of mice bearing, these tumors can be used directly to stimulate $T_d$ production. But IgD can also be isolated from such media and ascites and used in purified form to stimulate $T_d$ production.

Use of purified IgD is preferable for therapeutic or vaccine applications.

IgD can be purified by immunoaffinity chromatography using anti-IgD as the immunoadsorbent.

Such anti-IgD are commercially available. For example, anti-(mouse IgD) can be obtained from Miles Laboratories, Naperville, Ill. and anti-(human IgD) can be obtained from Cooper Biomedical, Melvern, Pa. or Boehringer-Mannheim Biochemicals, Indianapolis, Ind.

Purified IgD or an IgD-containing fluid can then be used to elicit $T_d$ in vitro or in vivo. T lymphocytes that are preferably histocompatible with the target host should be exposed to amounts of IgD that are greater than those available in the bloodstream or lymph of the host.

A particularly preferred regimen for $T_d$ induction or use of IgD as an adjuvant, in mice, is two to four intraperitoneal injections of 0.5 ml of IgD-containing ascites fluid given 7 and 1, or 8, 7, 6 and 5 days before challenge with antigen, respectively. Enhancement of immune response is more pronounced if the $T_d$ are induced in the recipient prior to injection of antigen.

When purified IgD is used for $T_d$ elicitation or adjuvant use in mice, 250 micrograms of affinity-purified IgD per day in 0.5 ml saline are effective when used on the 8th, 7th, 6th, and 5th day (or on the 7th and 1st day) before antigen challenge, but the minimum effective dose still needs to be established. However, this can be done by routine experimentation using serially diluted preparations of IgD.

When $T_d$ are induced in vivo, it is desirable to use the minimum amount of IgD capable of eliciting the maximum number of $T_d$ (about 30% of the peripheral T population in mice and about 40% in man). Because this amount may vary from species to species (and may also vary somewhat from individual to individual), the minimum amount of IgD should be determined beforehand. Such determination is a matter of routine experimentation.

During in vitro elicitation of $T_d$, T lymphocytes from (or histocompatible with those of) the recipient are incubated (preferably overnight—although a substantial amount of $T_d$ effective to augment immune response is elicited even after incubation for one hour only) in IgD-coated dishes or in media containing IgD. Again, the minimum amount of IgD necessary for maximal $T_d$ induction (and immune response enhancement) can be determined by testing the incidence of $T_d$ cells by serially diluted IgD.

Preferred concentrations of purified IgD and IgD-containing ascites fluid for mouse $T_d$ induction in vitro are: from 0.08–25 micrograms/ml and 0.1 to 10%, most preferably about 25 micrograms/ml and 10%, respectively.

For humans, preferred concentrations are expected to range from about 10 to about 250 micrograms/ml.

The most preferred incubation time for mammals is about 12–18 hrs but an acceptable $T_d$ response can be obtained in as little as one hour.

The $T_d$ thus elicited will be washed and introduced to the recipient. For mice, about $5 \times 10^6 - 5 \times 10^7$ cells in saline are preferred.

Preliminary data show that T cells from aging (immunodeficient) mice are much less responsive to one exposure to IgD in vitro, i.e., no significant $T_d$ are observed. Therefore, it is possible that the present invention can be used to test the ability of T cells to acquire IgD receptors, and thus diagnose the presence of an immune deficiency, or immune incompetence. Thus, the present invention forms the basis for development of an assay for that purpose.

Normal Balb/c spleen cells (fresh, or incubated in medium alone) show minimum IgD-RFC(5% or less).[1] But after incubation with IgD-containing medium for 18 hrs, the percentage of RFC increases to more than 25%. The same is observed for splenic T cells. Similar increases in the frequency of IgD-RFC also occur following incubation for 1 hour of isolated T cells in IgD-coated petri dishes. The rosette-forming ability of the IgD-exposed T cells is inhibited by pre-incubation of the cells in IgD, or by the presence of competing IgD in the liquid phase during the assay, but not by competing IgM or IgG.

[1] "IgD-RFC" means rosette forming cells, i.e. T cells that aggregate in rosette fashion with IgD-coated indicator cells.

The results of in vitro elicitation of $T_d$ are comparable to those obtained by in vivo injection of IgD or IgD-ascites. In comparative experiments, the number of $T_d$ after in vitro exposure to IgD was about 28%, and that of in vivo produced $T_d$ was about 30% for mice.

The murine $T_d$ cells of the present invention have been characterized. At least a majority of them are of the Lyt1+2− (helper) T-cell phenotype. This is in contrast to $T_a$ and $T_e$ cells of the prior art that are frequently of the suppressor phenotype.

The present inventors have found that the ability to respond to IgD with increased numbers of IgD-RFC appears to be exclusive in mature T cells. Thymocytes (immature T cells) do not have this ability to any significant extent.

The RFC ability of T cells is not allotype-specific. Therefore, $T_d$ can be elicited by exposure of these cells to IgD of a different allotype. $T_d$ cells thus obtained can be used to enhance immune responses.

The appearance of $T_d$ cells coincides with the ability to enhance the immune response. However, the magnitude and kinetics of the two phenomena differ somewhat. As illustrated in Example 6, the percentage of mouse $T_d$ in vivo rises to near maximum one day after IgD injection, falls to background levels by day 3 and then rises again to maximal levels by day 5. If a second IgD injection is given, the number of $T_d$ does not exceed this maximum.

In contrast to the $T_d$ number, the immune response increases simultaneously with the number of $T_d$ after the first IgD injection, but increases again after the second IgD injection, whereas the $T_d$ number stays the same. Therefore, maximal augmentation of the immune response in vivo and, in particular, augmentation of the IgG response requires more than one injection with IgD. A hypothesis that re-exposure to IgD increases the avidity of the $T_d$ cells for IgD, either by increasing the number of receptors or their affinity, provides an explanation for this phenomenon.

The present invention may be advantageously combined with other methods known to enhance immune respone, such as infusion of lymphokines, addition of carrier-primed T cells in vitro, etc.

The present invention is further described below by reference to specific Examples, which are intended to illustrate the present invention without limiting its scope. In fact, although this invention is described in this application by reference to preferred embodiments, persons of ordinary skill in the field will readily recognize that several additions, omissions or modifications can be made in the methods and materials described here, without departing from the spirit and scope of the present invention, as claimed in this application.

EXAMPLE 1:

Source and Purification of IgD.

IgD was isolated from the ascites fluid of mice bearing IgD-secreting plasmacytomas, such as TEPC-1017 or TEPC-1033 prepared as described by Finkelman, F.C. *J. Immunol.* 123-1253, 1979. Large numbers of IgD-secreting tumor or hybridoma cells can be grown in culture or, preferably, by transplantation (intraperitoneally) as was done here.

Balb/c mice were intraperitoneally injected with $10^6$ TEPC-1017 cells. Ascites tumor was evident in 10 days. Two weeks after injection, ascites fluid was drawn and examined for IgD content by double diffusion in agar using a highly specific goat anti-(mouse IgD), in accordance with the method described in *Methods in Immunology*, W. A. Benjamin, Inc. (Reading, Ma.), J. S. Garvey et al Eds. 1977 (pp. 313-321).

IgD-positive ascites fluid was collected and IgD was purified from it by immunoaffinity chromatography on a Sepharose 4B column (Pharmacia Fine Chemical Co. Uppsala, Sweden) using rabbit anti-(mouse IgD) as an immunoadsorbent. After extensive washing with phosphate buffered saline (PBS) pH 7.2, the IgD was eluted with 4.0M $MgCl_2$. The eluate was dialyzed and reconstituted in PBS to the same volume as the original ascites fluid.

EXAMPLE 2:

Specificity of IgD-Rosette Forming Cells by Exposure to IgD in Vitro

Spleen lymphocytes were obtained from Balb/c mice (Charles River Breeding Laboratories, Inc. Wilmington, Mass.). Single-cell suspensions were prepared. Splenic T cells were purified by negative selection, as follows:

Petri dishes were coated with affinity-purified goat-anti mouse Ig (such anti-Ig are available from Miles-Yeda Laboratories, Elkart, Ind.). Spleen lymphocytes were panned on the dishes and incubated for 1 hr under conditions favoring binding of B-cells to the antibody. The unbound cells were removed, washed and collected for use. The percentage of Ig+ cells contaminating such purified T-cell suspensions following this T-cell enrichment procedure was consistently lower than 1%. The splenic T-cell purification method was that of Wysocki, L.J. and Sato, V.L., *Proc. Nat'l Acad. Sci.* (USA) 75:2844 (1978).

Spleen cells and splenic T-cells purified as described above ($2.5 \times 10^6$ cells in each case) were separately incubated at 37° C. for 18 hr in 1 ml of minimum essential medium (MEM from GIBCO, Grand Island, N.Y.) containing 2% fetal calf serum (FCS). The medium was used alone (as a control) or supplemented with a 1:10 dilution of IgD-containing TEPC-1017 ascites fluid that contained about 30 micrograms IgD/ml; 0.04-20 micrograms/ml of purified IgD from Example 1; or 10% (IgM+IgG)-containing ascites fluid obtained from mice bearing the MOPC 104E plasmacytoma available from the NCI Tumor Bank. The MOPC 104E plasmacytoma was grown by ascites tumor induction in a way analogous to that described in Example 1 for the TEPC-1017 plasmacytoma.

After the incubation period the cells were washed twice in MEM, suspended in fresh MEM containing 2% FCS, and used in the RFC (Rosette-Forming Cell) assay.

IgD was affinity-purified from ascites fluid of Balb/c mice bearing IgD-secreting myeloma TEPC-1017 as described in Example 1. The IgD was coupled to sheep erythrocytes (SE) using chromium trichloride according to the well-known method of Poston, R.N. *J. Immunol. Meth.* 5:91 (1974), incorporated by reference.

Coupling of IgD to SE was confirmed by positive hemagglutination and indirect immunofluorescence assay using rabbit anti-mouse IgD anti-serum which can be obtained from Miles-Yeda, supra). The well-known passive hemagglutination method of Bogden, S.V. *J. Exp. Med.* 93: 107 (1951) was used except that $CrCl_3$ was used (instead of tannic acid) to couple IgD protein to the sheep erythrocytes. Indirect immunofluorescence was performed by staining IgD-coated sheep erythrocytes, (which were preincubated for 15 min. with rabbit anti-mouse IgD, then washed twice in MEM) with fluorescein-labeled goat anti-rabbit gamma globulin (Miles-Yeda Laboratories, Elkart, Ind.). Postively stained cells were scored using a fluoresence microscope.

The RFC assay was performed as follows: 0.2 ml of 1% IgD-SE in MEM were incubated with 0.1 ml of the spleen or splenic T cells ($2.5 \times 10^6$ cells/ml) for 15 min. at 37° C. Competing Ig-containing ascites are added in selected experiments (see Table 1). The cells were centrifuged at 500 rpm (200 xg) for 5 minutes and further incubated at 4° C. for 45 min. or overnight. Samples containing competing IgD-containing or (IgM+IgG)-containing ascites fluid to a final concentration of 6% were included in the assay. This method of IgD-RFC scoring is based on a method of Chen, S et al, *J. Immunol.* 127-166 (1981).

The lymphocytes were stained with 0.025 ml of a 1% toluidine blue (Fisher Scientific Co., Fairlawn, N.J.) solution immediately before scoring.

Lymphocytes surrounded by more than 3 indicator cells were scored as rosettes and the results expressed as percent RFC. The background rosette formation was determined in each experiment and was always found to be less than 2%.

The results are summarized in Table 1. The results of the Students' t-test analysis are given for each assay. Fresh, normal Balb/c spleen cells (controls) show 5 ±0.8% IgD-RFC (n=15). After incubation in medium alone or in medium with IgM and IgG for 18 hrs, this percentage does not change significantly. After incubation with IgD the percentage of IgD-RFC is >25%. Inclusion of IgD in the medium during the RFC assay competes and therefore inhibits rosette formation (line 3), whereas inclusion of IgM and IgG does not (line 4).

TABLE 1

| Cells | Immunoglobulin-Containing Ascites Added During Assay | Mean Percent IgD-RFC ± S.E.(n) Following Incubation With | | | |
|---|---|---|---|---|---|
| | | Medium Alone | Medium and IgD-ascites | Medium and Purified IGD | Medium and (IgG)-(IgM + IgG)-Ascites |
| Unfrac- | — | 8 ± 0.7(9)[a,b] | 27 ± 1.6(10)[a] | 29 ± 1.9(19)[b] | 6 ± 1.3(3) |

TABLE 1-continued

| Cells | Immunoglobulin-Containing Ascites Added During Assay | Mean Percent IgD-RFC ± S.E.(n) Following Incubation With | | | |
|---|---|---|---|---|---|
| | | Medium Alone | Medium and IgD-ascites | Medium and Purified IGD | Medium and (IgG)-(IgM + IgG)-Ascites |
| tionated Spleen | | | | | |
| Splenic T | — | 9 ± 0.8(4)$^{c,d}$ | 31 ± 3.0(4)$^{c,e}$ | 27 ± 1.2(8)$^d$ | 7 ± 0.9(6) |
| Splenic T | IgD | — | 6 ± 2.5(3)$^e$ | — | — |
| Splenic T | IgM ± IgG | — | 30 ± 0.05(3) | — | — |

$^a$p < 0.0001,
$^b$p < 0.0001,
$^c$p = 0.001,
$^d$p < 0.0001,
$^e$p = 0.001

EXAMPLE 3

In Vitro Induction of $T_d$ Cells Following Exposure to IgD

The RFC assay of Example 2 was repeated using different types of lymphocytes with such modifications as described below.

Spleen lymphocytes and splenic T-cells were obtained as for Example 2. Splenic Lyt1+2− and L3T4− T-cell subpopulations were isolated by complement-mediated cytolysis using the monoclonal antibodies anti-Lyt2.2 (available from ATCC) and anti-L3T4 (GK1.5) (obtained from a private source, Dr. F. Fitch, University of Chicago, Ill.) as follows:

Splenic B cells were also used. They were purified by complement-mediated cytolysis of T-cells, but using a cocktail of anti-Thy1.2 (6.80) (from ATCC), anti-Lyt1.2(C2P0) and anti-L3T4 (GK1.5). The latter were obtained from Dr. V. Hammerling, Sloan-Kettering Institute, New York City.

All the cells were from Balb/c mice except for one batch of C.B20 spleen cells (Charles River Laboratories, Wilmington, Mass.). The C.B20 cells were included to see if the assay was allotype specific, which it was not.

Some of the spleen cells came from mice that had been pretreated in vivo by injecting them either intravenously with 100 micrograms TNP-KLH (5 days prior to the day of the assay) or twice intraperitoneally with 0.5 ml of IgD-containing ascites fluid (7 and 1 days prior to the assay).

All cells were incubated for 18 hrs in medium alone or in medium containing IgD-ascites fluid, as described in Example 2. The results, representing arithmetic means of data from 3–6 assays, are set forth in Table 2, below. Values of p in Tables 1 and 2 were computed by comparing the mean percentage of IgD-RFC following overnight incubation with the mean percentage of RFC for splenic T-cells following overnight incubation in medium alone.

TABLE 2

| Cell Type | In Vivo Pretreatment | Mean Percent of IgD-RFC ± S.E. After Overnight Incubation With | | p |
|---|---|---|---|---|
| | | Medium | IgD-containing ascites | |
| Spleen | — | 8 ± 1.2 | 28 ± 1.9 | <0.0001 |
| Spleen | TNP-KLH | 11 ± 1.7 | 20 ± 2.4 | 0.001 |
| Spleen | IgD-ascites | 30 ± 1.7 | 31 ± 2.4 | n.s. |
| Splenic T | — | 8 ± 0.7 | 30 ± 2.9 | 0.01 |
| Splenic T(Lyt1+2−) | — | | 40 ± 2.1 | <0.0001 |
| Splenic T(L3T4−) | — | | 8 ± 1.9 | n.s. |
| Splenic B | — | 5 ± 0.7 | 8 ± 1.4 | n.s. |
| Lymph node | — | 5 ± 0.9 | 42 ± 3.9 | 0.006 |
| Thymocytes | — | 5 ± 0.3 | 8 ± 1.5 | n.s. |
| C.B20 Spleen | — | 8 ± 0.5 | 31 ± 2.2 | <0.0001 |

EXAMPLE 4

Phenotype of T Cells that Recognize IgD.

The results of Example 3 suggest that the majority (if not all) of the IgD-RFC induced in vitro have the helper T cell phenotype. To determine whether the same population responds in vivo to injection of IgD, spleen, splenic T and Lyt1+2− splenic T cells, lymph node cells, and thymocytes from IgD pretreated mice were tested for ability to form IgD-RFC. Trinitrophenylated keyhole limpet hemocyanin-primed spleen cells (from mice immunized with 100 micrograms of TNP-KLH five days prior to the day of the assay) and unprimed spleen cells were used as controls. TNP-KLH was prepared by Little, J.R. and Eisen, H. N. *Methods Immunol. Immunochem.* 1:128 (1967). TNP was purchased from Sigma Chemical Co., St. Louis, Mo. Keyhole limpet hemocyanin was obtained from Schwarz/Mann Div., Becton Dickinson & Co., Orangeburg, N.J.

All cells were obtained from Balb/c mice and purified, as described above. Where indicated in Table 3, cells were used from mice that had been injected with 0.5 ml of IgD-containing ascites fluid 7 and 1 days prior to the day of the assay. Control cells were not exposed to IgD-ascites.

The RFC assay was performed as described in Examples 2 and 3.

The results are summarized in Table 3 below.

TABLE 3

| Cell Type | In Vivo Pretreatment with IgD-Containing Ascites Fluid | Mean % IgD-RFC ± S.E.(n) | P |
|---|---|---|---|
| Spleen | + | 23 ± 1.4 (8) | |
| " | − | 5 ± 0.8 (6) | <0.0001 |
| Splenic T | + | 30 ± 4.7 (5) | 0.02 |

TABLE 3-continued

| Cell Type | In Vivo Pretreatment with IgD-Containing Ascites Fluid | Mean % IgD-RFC ± S.E.(n) | P |
|---|---|---|---|
| " | − | 4 ± 0.4 (4) | |
| Lyt1+2− Splenic T | + | 27 ± 1.3 (5) | <0.0005 |
| Ly+− Splenic T | − | 5 ± 0.3 (3) | |
| Lymph node | + | 32 ± 2.5 (5) | <0.005 |
| " | − | 12 ± 1.3 (4) | |
| Thymocytes | + | 3 ± 2.5 (4) | n.s. |
| " | − | 5 ± 0.5 (4) | |
| TNP-KLH primed spleen | − | 12 ± 1.2 (7) | <0.005 |
| Unprimed spleen | − | 5 ± 0.6 (7) | |

EXAMPLE 5

Ability of Splenic T Cells to Transfer the Immune Response-Enhancing Effect of IgD-Ascites Pretreatment to Untreated Recipients.

Spleen cells or splenic B or T cells ($10^7$) from mice pretreated with IgD-containing ascites or purified IgD (as described in Example 2) were injected simultaneously with TNP-KLH (100 micrograms) into recipients that had been irradiated one day before injection with 100R of gamma irradiation using a $^{137}$Cs source (from Isomedix, Parsipanny, N. J.). Cells from mice that had not been pretreated with IgD were used as controls.

The cells used for injection were purified as in Examples 2 and 3.

The spleens of the mice were assayed for plaqueforming cells (PFC) on day 5 after injection. The assay employed was as follows:

Spleen cells were suspended in Hanks' balanced salt solution (Gibco Laboratories, Grand Island, N.Y.).

Enumeration of PFC was performed using the well-known method of Jerne, N.K. et al (in *Cell-Bound Antibody*, Amos, B. and Koprowsky, H. Eds, Wistar Institute Press pp. 109-111, 1983) with the slide modification of Mishell, R. I. and Dutton, R.W. J. Exp. Med. 126–423, 1967, both incorporated by reference.

TABLE 4

ABILITY OF SPLENIC T CELLS TO TRANSFER THE IMMUNOENHANCING EFFECT OF IgD

| Expt. | Donor Cells Transferred[a] | Preinjection of Donors with IgD | (Geometric Mean X/÷ (S.E.) of Anti-TNP PFC/Spleen[c] |
|---|---|---|---|
| 1 | None | | 2,230 ×/÷ (1.4) |
| | Spleen Cells | − | 3,950 ×/÷ (1.3)[h] |
| | | + | 12,320 ×/÷ (1.2) |
| 2 | Spleen Cells | − | 3,400 ×/÷ (1.4)[ij] |
| | | + | 14,760 ×/÷ (1.1)[i] |
| | | +[e] | 11,060 ×/÷ (1.1)[j] |
| | Splenic T/ Cells[d] | − | 3,984 ×/÷ (1.2)[l] |
| | | + | 13,378 ×/÷ (1.2)[l] |
| | Splenic B/ Cells[f] | − | 3,840 ×/÷ (1.2)[k] |
| | | + | 4,370 ×/÷ (1.1)[k] |

[a]Recipients were irradiated on day-1 with 100R, and then injected iv on day 0 with $10^7$ donor cells together with 100 micrograms TNP-KLH. Anti-TNP PFC responses were determined on day 5 (n = 5–8).
[b]Donor mice were preinjected ip with 0.5 ml of IgD-containing ascites fluid on days-8,-7,-6 and-5 relative to the day of sacrifice (day 0).
[c]19S anti-TNP PFC responses, geometric mean S.E.
[d]T cells were prepared by panning on anti-Ig-coated dishes at 4° C. after removal of adherent cells at 37° C. Control cells were simultaneously incubated on uncoated dishes.
[e]Donors were injected ip with 250 micrograms affinity-purified IgD on days-8,-7,-6 and -5.
[f]B cells were prepared by anti-Thy1.2 plus complement treatment, control.
[h]p = 0.007.
[i]p = 0.005.
[j]p = 0.01.
[k]Not significant.
[l]p = 0.005.

As shown in Table 4, the anti-TNP plaque-forming cell responses are significantly higher in recipients of IgD-treated cells than in recipients of untreated control cells. The effect is due to the IgD, since it is present when purified IgD is used as the T-cell treating agent.

The above results demonstrate that the immunoaugmenting effect of IgD is mediated by T cells and that it can be transferred by T cells to another recipient that has not been exposed to IgD. Thus, injection of IgD in the target host is not essential for the present invention.

EXAMPLE 6:

Relative Kinetics of $T_d$ Cells and Immune Response Augmentation

Balb/c mice were injected with 0.5 ml of IgD-containing ascites fluid on days -7, -5, -3, and -1 before priming with TNP-KLH (100 micrograms). Five days later, the anti-TNP plaque-forming PFC responses were measured, as in Example 5. IgG-producing cells (7S response) were developed with a rabbit anti-(mouse Ig) in the complement and goat anti-mouse IgM in the agar. Both immunoglobulins were obtained from Cooper Biomedical. The results, expressed in percent of control responses x/÷ S.E., are shown in FIG. 1A. The results are given for both 7S (IgG) and 19S (IgM) responses.

Spleen cells were also obtained on the day of TNP-KLH challenge and the percentage of IgD-RFC was determined. The results are shown in FIG. 1B.

EXAMPLE 7

Ability of T Cells Incubated in IgD-coated Petri Dishes to Augment Antibody Response CBA/J Splenic T cells were isolated by negative selection on petri dishes coated with goat anti-(mouse Ig) as described in Example 5. T cells ($3 \times 10^7$ cells/4 ml PBS) were incubated for 1 hr. in 100 mm bacteriological grade petri dishes that had been coated with IgD from the ascites fluid of a mouse bearing a transplanted TEPC 1017 plasmacytoma. Coating took place as follows:

Bacteriological grade, 100 mm petri dishes (Fisher Scientific Co., Pittsburgh, Pa.) were coated for 1 hr at room temperature with 10 ml Tris buffer, pH 9.5, containing 6 mg of ascites protein from either the TEPC-1017 or MOPC-167 plasmacytoma. Following 3 washes with PBS containing 2% FCS, $3 \times 10^7$ T cells suspended in 4 ml of PBS were added and the plates were further incubated at 37° C. for 1 hr. Following this incubation procedure, cells were vigorously triturated to remove them from the dish and the harvested cells were washed 3 times with PBS.

Cell preparations (in 0.2 ml saline) were injected i.v. in mice ($10^7$ cells/recipient) simultaneously with TNP-KLH (100 micrograms). Spleen cells were obtained from these mice and subjected to the PFC assay as described in Example 5. The results were as follows:

co-administered to the recipient mice. Their anti-TNP PFC responses were determined. The results for both IgG and IgM responses are shown in Table 6, expressed as geometric mean $x/\div$ S.E. (n=3-7). The results of this experiment demonstrate that the transferable augmentation of immune response continues to increase if the donor cells from IgD-preinjected mice are incubated with IgD prior to injection in the recipient mice.

TABLE 6
EFFECT OF IN VITRO EXPOSURE TO IgD
ON THE IMMUNE AUGMENTING T CELLS

| | | TNP-PFC/Spleen in Recipients of:[a] | | | | | |
|---|---|---|---|---|---|---|---|
| | Donor Cells | Expt. 1 Whole Spleen Cells | | Expt. 2 Splenic T Cells | | Expt. 3 Splenic T Cells | |
| Donors | Incubated in: | 19S | 7S | 19S | 7S | 19S | 7S |
| Normal Mice | Uncoated dishes | 3,400(1.4)[c,i] | 1,200(1.3)[d,j] | 45,100(1.1)[g] | 35,300(1.1)[h] | — | — |
| | TEPC-1017 (IgD)-coated dishes | 11,400(1.4)[c,k] | 6,700(1.0)[d,l] | 51,400(1.1)[m] | 62,900(1.1)[h,n] | — | — |
| | MOPC-167A (IgA)-coated dishes | — | — | 15,000(1.1)[g] | 23,400(1.1) | — | — |
| | No cells transferred | — | — | 33,000(1.2)[m] | 35,200(1.1)[n] | — | — |
| IgD-Preinjected Mice[b] | Uncoated dishes | 14,800(1.1)[i] | 6,700(1.3)[j] | — | — | 11,900(1.4)[e] | 2,800(1.3)[f] |
| | TEPC-1017 (IgD)-coated dishes | 18,600(1.1)[i] | 10,700(1.2)[l] | — | — | 17,900(1.1)[e] | 8,000(1.2)[f] |
| | MOPC-167A (IgA)-coated dishes | — | — | — | — | 11,900(1.1) | 2,600(1.2) |

[a]Recipients were irradiated with 100 R on day-1, then received $10^7$ donor cells on day 0 together with 100 ug TNP-KLH. Their anti-TNP PFC responses were determined and results are expressed as geometric mean $\times/\div$ S.E. (n = 3-7).
[b]Mice were injected i.p. with 0.5 ml of IgD-containing ascites fluid on days -8, -7, -6 and -5 prior to the day of sacrifice (day 0).
[c]p = 0.05;
[d]p = 0.05;
[d]p = 0.0005;
[e]p = 0.03;
[f]p = 0.01;
[g]p = 0.002;
[h]p = 0.006;
[i]p = 0.003;
[j]p = 0.002;
[k]p = 0.002;
[l]p = 0.035;
[m]p = 0.02;
[n]p = 0.006.

TABLE 5

| Donor Cells | Anti-TNP PFC/Spleen (Geometric mean $\times/\div$ S.E.) | |
|---|---|---|
| Incubated In: | 19S | 7S |
| uncoated petri dishes | 15,076 $\times/\div$ 1.1 | 15,568 $\times/\div$ 1.2 |
| IgD-coated petri dishes | 21,866 $\times/\div$ 1.1 | 34,641 $\times/\div$ 1.2 |
| No donor cells | 8,713 $\times/\div$ 1.1 | 18,448 $\times/\div$ 1.0 |
| | (p = 0.018) | (p = 0.008) |

EXAMPLE 8:

Effect of In Vitro Exposure to IgD on the Immune Augmenting Ability of T Cells Both IgD-preinjected and previously untreated Balb/c mice were used for this experiment as spleen and splenic-T cell donors.

The IgD-preinjected mice had been injected intraperitoneally with 0.5 ml of IgD-containing ascites fluid 8, 7, 6, and 5 days prior to the day of sacrifice, as described in Example 4. The mice were sacrificed. Spleen and splenic-T cells were obtained and cells of each type were incubated in IgD-coated dishes.

Uncoated and IgA-coated dishes were used as controls. The dishes were prepared and the cells were incubated as in Example 7.

The incubated cells were injected intravenously in recipient mice (syngeneic with the donor mice) that had been irradiated with 100R of gamma-irradiation one day prior to cell transfer. TNP-KLH (100 micrograms) was

EXAMPLE 9:

In Vitro Induction of Human Peripheral Blood Leukocyte IgD-RFC

Peripheral blood leukocytes (PBL) were isolated by layering over ficoll-hypaque (Lymphoprep Accurate Chemical Co., Hicksville, N.Y.). The PBL ($2.5 \times 10^6$ cells) were cultured for 18 hrs in 1 ml of MEM containing 2% FCS in the presence or absence of purified IgD of myeloma origin purified by immunoaffinity chromatography. The IgD-RFC assay was similar to the one used for mouse cells except that purified human IgD-coated ox red blood cells were used as the indicator cells instead of sheep red blood cells. The results were as follows:

TABLE 6

| Concentration of IgD (ug/ml) | Mean % IgD-RFC |
|---|---|
| 0 | 3 |
| 15 | 5 |
| 30 | 10 |
| 60 | 15 |
| 125 | 20 |
| 250 | 18 |
| 500 | 19 |

The incidence of IgD-RFC in three additional individuals, where cells had been exposed to 500 μg IgD/ml was 54%, 38% and 33%, with corresponding background values of 4%, 4% and 15% for unexposed cells. The 15% background value was from an individual who had recently been immunized to hepatitis vaccine. In view of the fact that normal human peripheral blood contains only 10–15% B cells, 40% helper T and 20% suppressor/cytotoxic T cells, the high frequency of IgD-RFC in these experiments indicates that these RFC are helper T cells as they are in mice. Not all human IgD myeloma proteins are equally effective at inducing IgD-RFC in PBL. However, when mixed with a small amount of anti-IgD, these non-inducing IgD preparations become able to induce IgD-RFC.

EXAMPLE 10:

Inability of Spleen Cells from Aged Mice to Respond to IgD

As is well-known, aged mammals are immunodeficient. The experiment of Example 2 was repeated except that the experimental mice were aged. 10% IgD ascites was used in the incubation medium as described in Example 2, where indicated below. The results were as follows:

TABLE 7

| Age of Mouse (months) | IgD in Medium | IgD-RFC (Background Subtracted) |
|---|---|---|
| 2 | − | 1% |
|   | + | 30% |
| 3 | − | 1% |
|   | + | 25% |
| 3 | − | 1% |
|   | + | 32% |
| 21 | − | 1% |
|   | + | <1% |
| 22 | − | 4% |
|   | + | <1% |
| 22 | − | 5% |
|   | + | <1% |
| 22 | − | 2% |
|   | + | 3% |

The aged mouse cells did not respond to incubation with IgD. However, repeated injection of IgD would elicit $T_d$ cells from these mice as well, especially if administered together with lymphokines.

The invention is further illustrated below by the following paper examples.

PAPER EXAMPLE 11:

Immune Response Enhancement in Immunologically Immature Mammals

Since neonatal mammals, like aged mammals, are immunodeficient, the following experiment will be performed in Balb/c mice. Mice of varying ages will be examined (a) for expression of IgD on B cells, (b) for ability of T cells to express T receptors after incubation with IgD. Ages to be examined will include: 1, 2, 3, 4 and 6 week old as well as 8–12 week old mice as controls. Splenic T cells will be incubated with 25 μg IgD per ml for 18 hrs and assayed for incidence of IgD-RFC. B cells will be stained with anti-IgD to determine the percentage of surface IgD positive B cells. The ability of the T cells to respond with IgD receptor production will be compared with the ability of the mice to show immunoaugmented responses for 19S and 7S responses to TNP-KLH after injection of IgD in vivo. In addition, the ability of the T cells to express receptors for IgD at varying ages will be compared to the percentage of surface IgD positive B cells. This latter percentage is known to reach mature values by the age of 6 weeks.

Thus, the aim of these studies is to determine whether the immune maturation of the mice can be accelerated by injection of IgD and, if so, whether this is related to their ability to produce T cells.

If the mice up to ages 4–6 weeks do not respond with T production and show no enhancement of their immune responses after injections of IgD, they will receive transfer of T cells induced in T cells from adult normal syngeneic mice. The immune response of immature mice receiving normal adult T cells will then be compared with that of similar mice receiving T cells incubated with IgD in vitro.

This experiment will determine which percentage of IgD-bearing B cells is needed before an immunoaugmenting effect of T cells can be obtained.

PAPER EXAMPLE 12:

Detection of T cells in Human Peripheral Blood

Since it has been found that both age and recent immunization may affect the level of T cells, a convenient assay for T enumeration in man will be developed. Human peripheral blood cells will be prepared as in Example 9 and incubated with or without IgD for at least 1 hr. The cells will then be assayed for expression of IgD receptors by any of the following methods:

(1) IgD-RFC assay using IgD-coated indicators such as ox erythrocytes as described in Example 9 or IgD-coated latex particles as described in Sjoberg, supra.

(2) Incubation with a detectable specific ligand (ligand 1) for the IgD receptor. This can be done by labeling the ligand itself directly, or indirectly by using a labeled second ligand with specificity for ligand 1. Ligand 1 can be IgD itself or an antibody to the IgD receptor.

Labeling of ligands can for instance be done by the Biotinylation method described in: J. Immunol. Methods 36:335 (1980), or by the well-known Fluorescein-conjugation method described in: *Selected Methods in Cellular Immunology*, B. B. Mishell and S. M. Shiigi, eds., W. H. Freeman and Co. San Francisco, Calif., 1980, pp. 292–297, or by the well-known Peroxidase conjugation method of: Sternberger et al., J. Histochem. Cytochem. 18:315 (1970), or by the well-known enzyme marker protein linkage methods described by Avrameas, S., J. Histochem. 4:321 (1972).

These reagents are routinely used for methods employing the use of the fluorescence activated cell sorter (FACS).

What is claimed is:

1. A method for enhancing the ability of a mammal in need of such treatment to mount a 7S humoral response the method comprising:

obtaining lymphocytes histocompatible with the lymphocytes of said mammal;

at a location outside the body of the mammal to be treated, exposing said obtained T-lymphocytes to the presence of previously isolated, essentially purified polymeric or aggregated delta-immunoglobulin preparation at a concentration higher than that at which said lymphocytes would have been exposed while in the lymph or bloodstream of said mammal and for a time sufficient to induce the production of helper T-cells capable of stimulating the immune system of said mammal to produce IgG;

separating said lymphocytes from said IgD; and introducing said separated IgD-exposed lymphocytes to the bloodstream or lymph of said mammal.

2. The method of claim 1, wherein said induced helper T-cells have increased ability to bind IgD compared to helper T-cells that have not been so treated.

3. The method of claim 2, wherein said helper T-cell induction takes place in vitro.

4. The method of claim 2, wherein the helper T-cell induction takes place in vivo but not in the body of the treated mammal.

5. The method of claim 2, wherein said helper T-cell induction takes place both in vitro and in vivo, said in vivo induction taking place by administering to the mammal to be treated an amount of essentially purified polymeric or aggregated delta-immunoglobulin within the range of between about 0.08 and about 250 micrograms/ml.

6. The method of claim 3, wherein the lymphocytes are obtained from said mammal.

7. The method of claim 1, wherein said delta-immunoglobulin is obtained from a source selected from the group consisting of IgD-secreting tumor cells, IgD-secreting hybrid cells, mammalian plasma, and mammalian serum.

8. The method of claim 7, further comprising purifying said lymphocytes after said induction and prior to introducing them into said mammal.

9. The method of claim 7, comprising washing said lymphocytes to purify them.

10. A method of eliciting mammalian T-cells capable of inducing an enhanced 7S humoral immune response when administered to a mammalian host, said method comprising:

exposing T-cells in vitro to the presence of essentially purified polymeric or aggregated IgD at a concentration higher than that available to T-cells in the bloodstream or lymph of normal mammals for a period of time at least sufficient for a substantial portion of said T-cells to acquire an increased ability to bind IgD; and discontinuing said exposure of said T-cells.

11. The method of claim 10, said period of time being at least sufficient for a substantial portion of said T-cells to exhibit a receptor for IgD.

12. The method of claim 10, wherein said period of time is at least about one hour.

13. A method for enhancing the ability of a mammal to mount a 7S humoral immune response upon antigenic stimulation said method comprising:

exposing the lymphocytes of said mammal in vivo to an essentially purified, polymeric or aggregated IgD-containing preparation in an amount and for a period of time sufficient to activate helper T-cells and thereby enhance the subsequent production of a 7S isotype immune response;

administering an antigen to said mammal substantially contemporaneously with said IgD exposure;

discontinuing said IgD exposure;

subsequently repeating the administration of said antigen to said mammal; and waiting for said mammal to mount a 7S immune response.

14. The method of claim 13, wherein said exposure takes place by injection of said IgD preparation prior to immunization of said mammal with a vaccine, said preparation being in an amount sufficient to activate helper T-cells.

15. The method according to claim 13, wherein said exposure takes place by repeated injections of said IgD.

16. A method for enhancing the ability of a mammal to mount a humoral 7S immune response against an antigen comprising injecting in said mammal an essentially purified polymeric or aggregated IgD immunoglobulin preparation in an amount sufficient to augment the ability of helper T-cells to bind IgD, discontinuing IgD administration to said mammal and injecting in said mammal an antigen, thereby exposing the immune system of said mammal to said antigen in an amount sufficient for the mammal to exhibit an enhanced 7S immune response.

17. The method according to claim 16 further comprising:

obtaining lymphocytes from a donor IgD-treated mammal;

further exposing said lymphocytes to an essentially purified polymeric or aggregated IgD preparation in vitro; and infusing said in vitro-treated lymphocytes in said mammal.

18. A method for determining whether a mammal will respond with an enhanced 7S immune response after being treated with an essentially purified aggregated or polymeric IgD preparation, the method comprising:

exposing T-lymphocytes of said mammal to an essentially purified aggregated or polymeric IgD preparation in an amount previously determined to be sufficient to elicit helper T-cells with an ability to bind IgD in normally immunocompetent mammals of the same species;

discontinuing said exposure by washing said cells;

detecting among said lymphocytes the numbers of helper T-cells with said ability formed with and without said IgD exposure; and comparing said numbers to those of normal immunocompetent mammals to see whether said numbers are comparable to those of said normal mammals.

19. The method of claim 13, wherein said exposure takes place by injection of said essentially purified aggregated or polymeric IgD preparation simultaneously with immunization of said mammal with a vaccine, said preparation being in an amount sufficient to activate helper T-cells to mediate augmentation of humoral immune response of more than one isotype.

20. The method of claim 13, wherein said exposure takes place by injection of said IgD both prior to and simultaneously with said immunization.

21. The method of claim 13 wherein said exposure to said IgD is preceded by, followed by, or combined with in vivo treatment of said mammal with interleukin-2.

* * * * *